United States Patent
Ljungquist

(10) Patent No.: US 6,773,414 B2
(45) Date of Patent: Aug. 10, 2004

(54) DEVICE AND METHOD FOR DISPENSING AT LEAST TWO MUTUALLY REACTIVE COMPONENTS

(75) Inventor: Olle Ljungquist, Vallentuna (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 10/047,322

(22) Filed: Jan. 14, 2002

(65) Prior Publication Data
US 2002/0138038 A1 Sep. 26, 2002

(30) Foreign Application Priority Data
Jan. 12, 2001 (SE) .............................. 0100091

(51) Int. Cl.⁷ .................. A61M 37/00; A61M 3/30; A61B 17/08
(52) U.S. Cl. .................. 604/82; 604/70; 606/213
(58) Field of Search .................. 604/82–89, 70, 604/15, 285, 506, 191, 960.01; 606/214, 213; 128/898; 239/10, 424–425, 79; 222/145.1

(56) References Cited

U.S. PATENT DOCUMENTS

| | | | | |
|---|---|---|---|---|
| 4,978,336 A | * | 12/1990 | Capozzi et al. | 604/82 |
| 5,605,541 A | | 2/1997 | Holm | 604/82 |
| 5,800,538 A | * | 9/1998 | Slepian et al. | 128/898 |
| 6,033,427 A | * | 3/2000 | Lee | 606/213 |
| 6,179,862 B1 | * | 1/2001 | Sawhney | 606/214 |
| 6,331,172 B1 | * | 12/2001 | Epstein et al. | 604/82 |
| 6,475,182 B1 | * | 11/2002 | Hnojewyj et al. | 604/82 |

FOREIGN PATENT DOCUMENTS

| | | |
|---|---|---|
| EP | 0 424 068 A2 | 4/1991 |
| EP | 0 858 755 A1 | 8/1998 |
| WO | WO 96/39212 | 12/1996 |

* cited by examiner

Primary Examiner—Brian L. Casler
Assistant Examiner—Roz Maiorino
(74) Attorney, Agent, or Firm—Fish & Richardson P.C.

(57) ABSTRACT

A device for dispensing at least two mutually reactive components, such as fibrinogen and thrombin, comprising a supplier (12A, 12B) having a primary channel for supplying a respective one of said at least two reactive components to a dispenser (14) having secondary channels (18A, 18B) for separately discharging said components at a distal end orifice thereof opening into a target area for external intimate mixing of the respective reactive components outside a distal tip end of said dispenser (14). A distributor (38, 40) is interposed between said supplier and said dispenser for multiplying the number of the respective primary channels with at least a factor 2. Adjacent ones of said secondary channels (18A, 18B) are adjoined to primary channels (32, 34) intended for supply of reactive components of different kind.

13 Claims, 2 Drawing Sheets

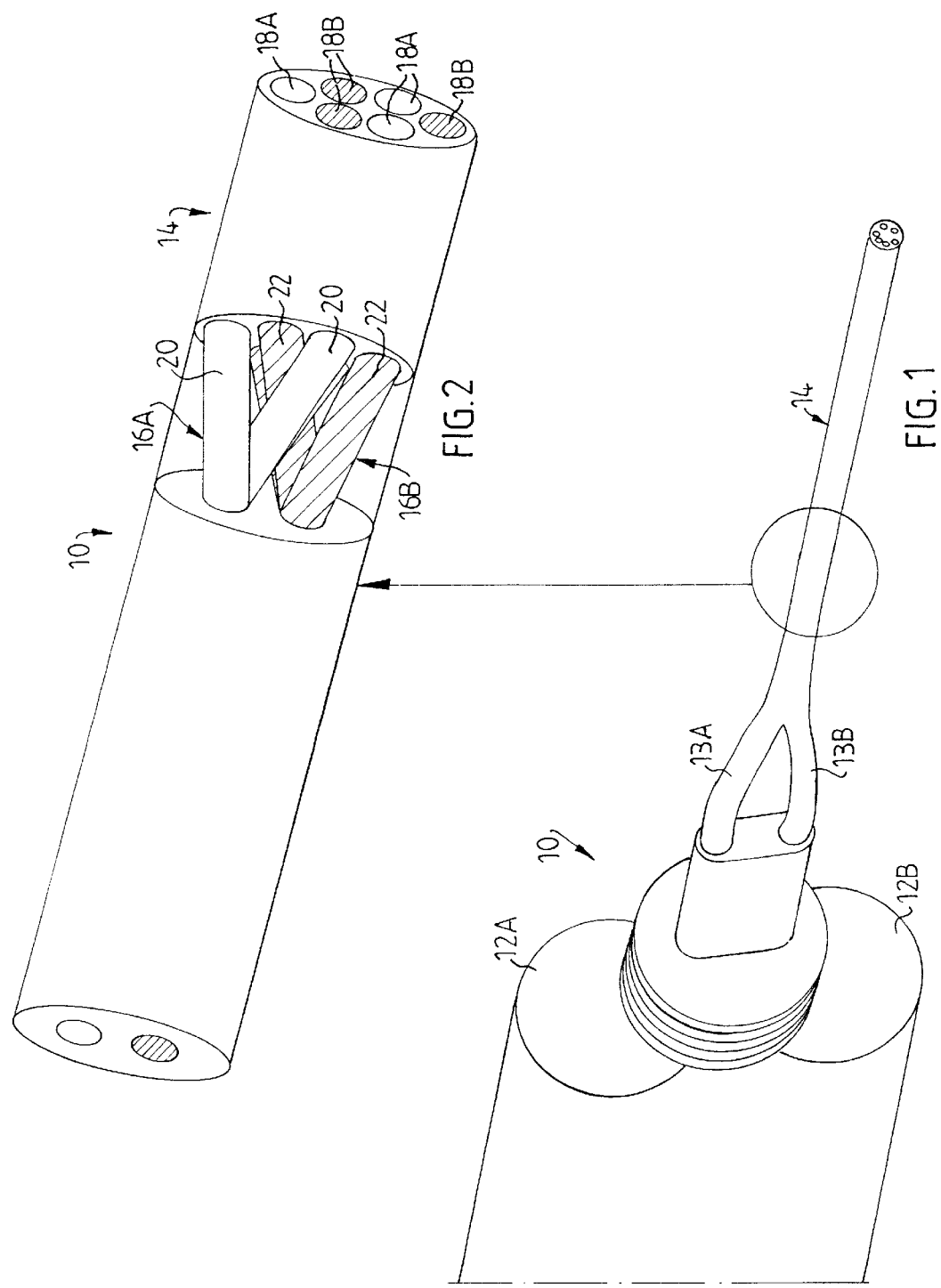

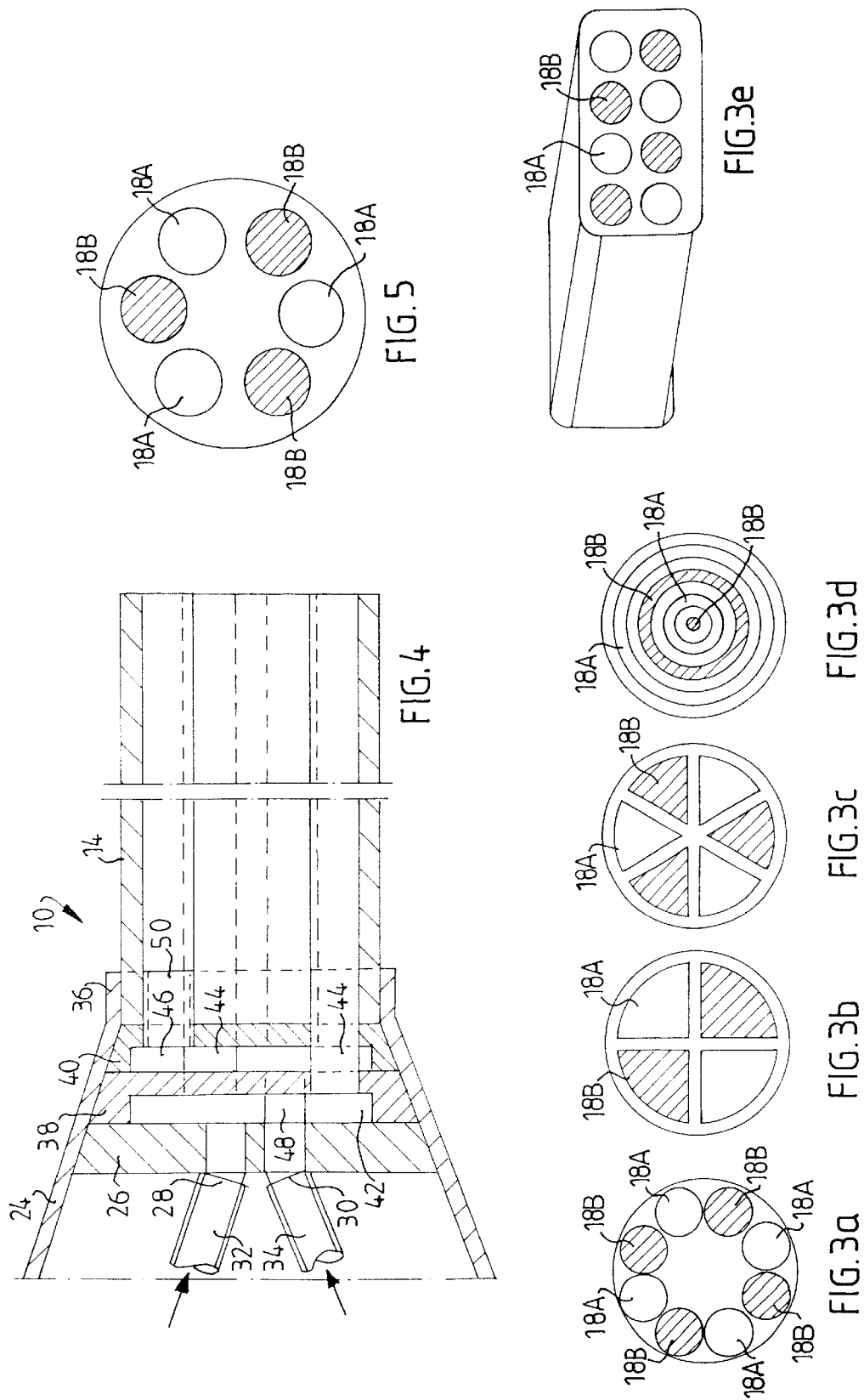

DEVICE AND METHOD FOR DISPENSING AT LEAST TWO MUTUALLY REACTIVE COMPONENTS

CROSS REFERENCE TO RELATED APPLICATIONS

This application claims priority from Swedish Patent Application No. 0100091-8, filed Jan. 12, 2001, the content of which is incorporated herein by reference in its entirety.

BACKGROUND OF THE INVENTION

1. Field of the Invention

The present invention relates in general to a device for dispensing at least two mutually reactive components. In particular, but not exclusively, the present invention is related to a device for applying an accurately mixed solution of reactive sealant components, such as fibrinogen and thrombin, to biological tissue, for example for effecting hemostasis or for achieving any other therapeutic objective.

The invention also relates to a method for dispensing at least two mutually reactive components.

2. Description of Related Art

Various kinds of apparatuses are known for applying a two-component sealant mixture of fibrin or fibrinogen and thrombin to a human tissue in order to stop bleeding or to close blood vessels.

For example, U.S. Pat. No. 5,322,510 discloses an injection-type apparatus for injecting at least two mutually reactive sealant components, wherein the apparatus comprises a hollow needle member having parallel, coaxially extending or side-by-side arranged lumens for each sealant component. The components are supplied to the injection needle through a corresponding number of hoses, which, at a proximal end thereof, are provided with syringe coupling connections for the supply of the respective reactive components. The distal end orifices of the lumens all lie in a common plane so that a mixing and a reaction of the components will commence as they emerge therefrom thereby forming a fibrin glue at the site of delivery. However, due to the fact that the number of outlet lumens are equal to the number of reactive components to be mixed, an optimal or sufficient mixing of the components will not always be ensured.

Many previously known devices for dispensing a mixture of various fluids, i.a. reactive liquids and gaseous media, (see, e.g., WO 97/17133, WO 00/18469, SE-B-432 059) are provided with at least two primary inlet channels for supplying respective fluids to be mixed to a mixing member which divides the fluid streams from the primary inlet channels into a plurality of smaller secondary fluid streams, which may cross each other at outlet orifices of the mixing member so as to be efficiently mixed in a separate mixing chamber downstream thereof before the mixture is delivered to the site of its application. However, in such devices clogging may occur in the mixing chamber and at the outlet opening thereof between the cycles of application, which necessitates either an ejection of the solidified material therein or a removal and change of the tip end piece before it can be reused.

EP 0 858 775 A1 discloses a fibrin sealant applicator (FIG. 15) for mixing two different fluid components, one supplied through a plurality of radially inwardly directed holes of a circular conduit, and the other supplied through a single axial orifice of a central conduit. This structure does not have a distributor between each primary component supplying channel and respective secondary component discharging channels, wherein each distributor multiplies the number of respective primary channels with at least a factor 2, such that adjacent ones of the secondary channels are adjoined to primary channels intended for supply of reactive components of different kind.

SUMMARY OF THE INVENTION

An object of the present invention is to solve the above-mentioned problems of the previously known devices and to provide an improved two- (or more) component applicator which is capable of dispensing a plurality of discrete adjacent streams of the components and to bring the same to be accurately mixed and cured at target site of application on various occasions and at timely spaced intervals without any clogging problems occurring at the outlet of the device.

According to the present invention these problems are solved by a device for dispensing at least two mutually reactive components, such as fibrinogen and thrombin, comprising a component supplier having a primary channel for supplying a respective one of said at least two reactive components to a component dispenser having secondary channels for separately discharging said reactive components at a distal end orifice thereof opening into a free target area for external intimate mixing of the respective reactive components outside a distal tip end of said dispenser, wherein a distributor is interposed between said supplier and said dispenser for multiplying the number of the respective primary channels with at least a factor 2, and adjacent ones of said secondary channels are adjoined to primary channels intended for supply of reactive components of different kind.

The method of the present invention for dispensing at least two mutually reactive components so as to allow for an intimate and accurate mixture and reaction thereof upon reaching a target site for their application is characterized by the steps of: feeding a primary flow of said at least two reactive components through respective primary conduits, and dispensing through distal end orifices of secondary conduits a plurality of secondary flows of said reactive components, derived from each of said primary flows of reactive components, in a pattern such that different reactive components are dispensed in close proximity through adjacent secondary conduit end orifices.

Other features and structural details of the device and the method of the present invention are disclosed in the following description and set forth in the accompanying dependent claims with reference to the attached drawings.

BRIEF DESCRIPTION OF THE DRAWINGS

FIG. 1 is a schematic perspective view of a first embodiment of a device of the present invention for dispensing two reactive sealant components.

FIG. 2 is an enlarged perspective view of the encircled section of the device in FIG. 1.

FIGS. 3a–e illustrate alternative outlet end orifice configuration of the inventive device.

FIG. 4 is a schematic, sectional side view of a further embodiment of a device of the present invention for dispensing two reactive sealant components.

FIG. 5 is an end view of the device in FIG. 4.

DESCRIPTION OF PREFERRED EMBODIMENTS

FIGS. 1 and 2 schematically show a first structural embodiment of a device 10 of the present invention for dispensing two reactive sealant components, such as fibrinogen and thrombin, for obtaining an intimate mixture of the respective reactive components immediately after exiting the distal outlet end of the device while avoiding clogging of sealant material within the device after a dispensing sequence. The device 10 comprises a component supplier in form of a first piston-activated supply container 12A and a second piston-activated supply container 12B which through two merging tubes 13A and 13B are adapted to supply a respective reactive fluid component (typically fibrinogen and thrombin) to an elongate tubular dispenser or applicator member 14 for separately discharging the components at a distal end thereof. In order to ensure an accurate and intimate mixture of the two reactive sealant components directly at a site for its application to human tissue the device is provided with a distributor 16A and 16B (FIG. 2) for distributing the supply of the sealant components from the respective container 12A and 12B and respective primary channels 17A and 17B to a plurality of respective secondary channels or lumens 18A and 18B being alternately separated in the circumferential direction of the tubular applicator member 14. In the embodiment shown in FIGS. 1 and 2, the distributor 16A and 16B thus multiply the number of each component supply flow with a factor 3, i.e., the flow of, e.g., fibrinogen from the container 12A is split into three flows in tubes 20, whereas the flow of thrombin from the container 12B is likewise split into three flows in tubes 22. As shown more clearly in FIG. 2, there are thus all together six channels or lumens 18A and 18B evenly separated circumferentially and alternately in the tubular member 14. Owing to the splitting up and a finely division of each main flow of reactive component into three secondary flows and allowing them to exit alternately and closely to one another as separate streams from free external distal outlet orifices of the lumens 18A and 18B, the secondary flows or streams of reactive components will create a well-defined sealant mixture at the target site where the two components are unified through diffusion without need for any additional mechanical mixing equipment. It should be noted that the mixing phase is not taking place in a mixing chamber defined by the device downstream of the outlet orifices where the subsequently solidified or cured sealant can clog the outlets of the tubular member 14 but in a free target area at the site of the application of the components, e.g. to human tissue where a bleeding is to be stopped.

The cross-section of the secondary channels 18A, 18B may have any suitable configuration, such as circular (FIGS. 2 and 3a and e), or sector-shaped (FIGS. 3b and c), or ring-shaped (FIG. 3d). The perimeter of the tubular applicator 14 is preferably circular but may have any other suitable configuration, such as rectangular (FIG. 3e). The number of secondary channels for each sealant component should be at least two (FIGS. 3b and d) but preferably three or more (FIGS. 2, 3a and 3c). The distal outlet orifices of the lumens 18A and 18B preferably lie in a common plane which may be normal or inclined to the longitudinal axis of the tubular member 14.

Furthermore, in order to obtain the desired well-defined mixture of the two components it is necessary to divide the two main flows from the containers 12A, 12B into fine part streams emitting from the distal end orifices of the lumens 18A, 18B. For this purpose the diameter of the lumens 18A, 18B and/or the distal end orifices thereof should, in dependence of the actual number thereof, generally lie within the interval 0.01–2 mm, preferably 0.05–1 mm, and most favorably 0.1–0.8 mm. Thus, in a suitable embodiment of the device of the present invention the diameter of the lumens 18A, 18B (or their orifices) may be 0.3 mm, in which case the outer diameter of the tubular applicator 14 is 1.7 mm. Preferably, the tubular applicator 14 is flexible so as to make it easier to reach more remotely located target areas, e.g. in various hollows of a human body.

In FIGS. 4 and 5 there is shown a second embodiment of a device for dispensing two mutually reactive sealant components according to the present invention. This embodiment comprises a connector housing 24 having a proximal insert piece 26 provided with two inlet fittings 28 and 30 for a respective tube 32 and 34. The tubes 32, 34 are, at a proximal end thereof, connected to a respective supply container or luer coupling (not shown) to which a respective syringe or the like may be connected for supplying a respective reactive fluid component, such as fibrinogen and thrombin. The housing 24 has a hub portion 36 to which a proximal end of an elongate tubular applicator member 14 having six secondary channels 18A and 18B—like in the embodiment of FIGS. 1 and 2—can be attached. In the housing 24, between the insert piece 26 and the proximal end of the tubular applicator member 14, there are mounted two elements 38 and 40 for distributing the respective fluid components from the inlet tubes 32 and 34 to the six corresponding secondary channels 18A and 18B such that, as shown in FIG. 5, the respective fluid components are evenly separated circumferentially and alternately in the tubular member 14. A first one 38 of said distribution elements has a collection chamber 42 for receiving a flow of, e.g., fibrinogen from the inlet tube 32 via the fitting 28, and three tubular outlet fittings 44 inserted into corresponding lumens 18A in the applicator member 14, whereas a second one 40 of said distributing elements has a collection chamber 46 for receiving a flow of, e.g., thrombin from the inlet tube 34 via the fitting 30 and a leading-in tube 48 extending through said first distributing element 38. The second distributing element 40 has likewise three tubular outlet fittings 50 inserted into corresponding lumens 18B in the applicator member 14. Also this embodiment provides a well-defined sealant mixture by diffusion outside the distal end of the tubular applicator member 14 without causing any clogging of solidified sealant material inside the secondary channels or lumens 18A and 18B.

What is claimed is:

1. A device for dispensing at least two mutually reactive components, comprising a component supplier having primary channels for supplying respective ones of said at least two reactive components to a component dispenser having secondary channels for separately discharging said at least two reactive components through orifices opening into a free target area at a distal tip end of the dispenser for external intimate mixing of the respective reactive components outside a distal tip end of said dispenser, wherein distributors are interposed between said primary and secondary channels for multiplying the number of each respective primary channel with at least a factor 2, adjacent ones of said orifices of said secondary channels being adjoined to said primary channels intended for supply of reactive components of different kind.

2. The device as set forth in claim 1, wherein each distributor comprises an inlet collection chamber communicating with respective secondary channels through at least two tubular branch fittings.

3. The device as set forth in claim 1, wherein each distributor comprises at least two branch tubes connecting each primary channel to the respective dispenser.

4. The device as set forth in claim 1, wherein said secondary channels are formed as elongate, parallel lumens extending side by side and evenly distributed circumferentially in a common cylindrical body.

5. The device as set forth in claim 4, wherein said lumens have a circular cross-section.

6. The device as set forth in claim 4, wherein said lumens have a segment-shaped cross-section.

7. The device as set forth in claim 1, wherein said secondary channels are formed as elongate, parallel lumens having a substantially annular cross-section and extending coaxially within a cylindrical body.

8. The device as set forth in claim 1, wherein said secondary channels are formed by a bundle of individual tubular elements.

9. The device as set forth in claim 1, wherein the device comprises six secondary channels.

10. The device as set forth in claim 1, wherein the device comprises eight secondary channels.

11. The device as set forth in claim 1, wherein the diameter of the secondary channels is between 0.01 and 2 mm.

12. The device as set forth in claim 11, wherein the diameter of the secondary channels is between 0.05 and 1 mm.

13. The device as set forth in claim 12, wherein the diameter of the secondary channels is between 0.1 and 0.8 mm.

* * * * *

UNITED STATES PATENT AND TRADEMARK OFFICE
CERTIFICATE OF CORRECTION

PATENT NO. : 6,773,414 B2
DATED : August 10, 2004
INVENTOR(S) : Olle Ljungquist

It is certified that error appears in the above-identified patent and that said Letters Patent is hereby corrected as shown below:

<u>Column 4,</u>
Line 55, insert -- of -- between "factor" and "2"
Line 58, replace "kind" with -- kinds --

Signed and Sealed this

Fifth Day of July, 2005

JON W. DUDAS
*Director of the United States Patent and Trademark Office*